United States Patent [19]

Meyer et al.

[11] 4,263,324
[45] Apr. 21, 1981

[54] ANTICOCCIDIAL AND OVOLARVICIDAL COMPOSITIONS

[75] Inventors: Alfred Meyer, Basel; Clemens Kocher, Therwil, both of Switzerland

[73] Assignee: Ciba-Geigy Corporation, Ardsley, N.Y.

[21] Appl. No.: 70,217

[22] Filed: Aug. 27, 1979

Related U.S. Application Data

[63] Continuation of Ser. No. 843,927, Oct. 20, 1977, abandoned.

[30] Foreign Application Priority Data

Oct. 27, 1976 [CH] Switzerland ............... 13541/76

[51] Int. Cl.$^3$ ............................................. A61K 31/13
[52] U.S. Cl. ................................ 424/325; 564/463; 564/488
[58] Field of Search .................................. 424/325

[56] References Cited

U.S. PATENT DOCUMENTS 3,226,293  12/1965  Ursprung ........................ 424/325
4,169,896  10/1979  Muntwyler et al. ............. 425/325

FOREIGN PATENT DOCUMENTS 131759  3/1969  Czechoslovakia ................ 424/325

OTHER PUBLICATIONS

Sevcik et al., Chem. Abst., vol. 83, abst. 172,292 b, (1975).
Sevcik et al., Veterinaria SPOFA, vol. 16, pp. 421-588, (1974).
Coccidiosis, pp. 453-456 and 468 to 472, Annals of the New York Academy of Sciences, vol. 52, published by the Academy, Nov. 1949, NY.
Encyclopedia Britannica, vol. 5, pp. 902-903, Encyclopaedia Britannica, Ltd., Chicago, U.S.A., (1961).
Ryley et al., "Chemotherapy of Chicken Coccidiosis", Advances in Pharmacology and Chemotherapy, vol. 11, pp. 221, 226, 227, 228, 288, and 289, (1973).
Singleton et al., Dictionary of Microbiology, pp. 95, 96, 114, John Wiley and Sons, N.Y. (1978).
Coccidiosis of Chickens, pp. 3-4, Noraid (Norwich Pharm. Co. Bulletin).

Primary Examiner—John D. Randolph
Attorney, Agent, or Firm—Frederick H. Rabin

[57] ABSTRACT

Compositions containing compounds of the formula

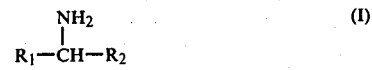

wherein
$R_1$ represents an alkyl radical of 4 to 24 carbon atoms and
$R_2$ represents hydrogen or an alkyl radical of 1 to 12 carbon atoms, and use of compounds of formula I for controlling coccidial and helminthic diseases.

6 Claims, No Drawings

ANTICOCCIDIAL AND OVOLARVICIDAL COMPOSITIONS

This application is a continuation of Ser. No. 843,927, filed Oct. 20, 1977, now abandoned.

DETAILED DISCLOSURE

The present invention relates to anticoccidial and ovolarvicidal compositions which contain aminoalkanes as active ingredients, and to a method of controlling coccidial and helminthic diseases which comprises the use of said compositions.

Coccidiosis is one of the most widespread diseases in numerous species of productive livestock, especially in poultry. It is caused by parasitic protozoa of the species Eimeria, for example *Eimeria tenella, Eimeria brunetti, Eimeria maxima, Eimeria necatrix, Eimeria, acervulina* etc. Animals attacked by coccidia have a poor increase in weight, with attendant intestinal bleeding and discharge of blood in their excrement. If the attack is severe, the coccidiosis results in high mortality among poultry. For poultry breeding it is therefore a matter of prime importance to provide suitable compositions for controlling this disease.

A particularly advantageous method of controlling coccidiosis consists in killing the oocysts excreted by the host animals. The oocysts are discharged with the excrement of the infected animals and remain viable for a considerable period of time, thus constituting a constant source of new infection.

Helminthiosis is also a frequent disease of productive livestock. It is caused by parasitic helminths, for example *Ascaris suum, Ascaridia galli* and *Toxocara canis*. Adult helminths attack mainly the digestive tract of the host animals and their primary stages migrate in the course of their development cycle into other organs, for example the lungs and the liver. Other species of helminths attack organs other than the digestive tract, for example the lungs, heart, kidneys, and the blood.

The eggs of the Ascarididae excreted by the host animals are protected by a thick shell and are very resistant to unfavourable environmental conditions, for example dryness or cold, and also to many chemicals. The eggs can survive for a number of years under suitable conditions and are the most difficult development stages of helminths to combat. However, the prevention of fresh infections caused by assimilation of the worm eggs is of considerable importance, for young animals in particular suffer great harm if the attack is severe.

It has now been found that aminoalkanes of the general formula I

wherein
$R_1$ represents an alkyl radical of 4 to 24 carbon atoms and
$R_2$ represents hydrogen or an alkyl radical of 1 to 12 carbon atoms;

act against both coccidial oocysts and eggs of the following species of Ascarididae: *Ascaris suum, Ascaridia galli* or *Toxocara canis*, whilst the excellent action against coccidial oocysts is to be singled out for special mention.

Compounds of the formula I in which $R_1$ represents a n-alkyl radical of 7 to 17 carbon atoms and $R_2$ represents hydrogen or an alkyl radical of 1 to 4 carbon atoms, have proved to be particularly effective against coccidial oocysts and Ascarididae eggs, and, within this group of compounds, in particular those in which $R_1$ represents a n-alkyl radical of 9 to 13 carbon atoms and $R_2$ represents hydrogen, methyl or ethyl.

A particularly pronounced anticoccidial and ovolarvicidal action is exhibited by compounds in which $R_1$ represents a n-alkyl radical of 9 to 12 carbon atoms and $R_2$ represents methyl or ethyl, or $R_1$ represents a n-alkyl radical of 11 to 13 carbon atoms and $R_2$ represents hydrogen, in particular by the following compounds:

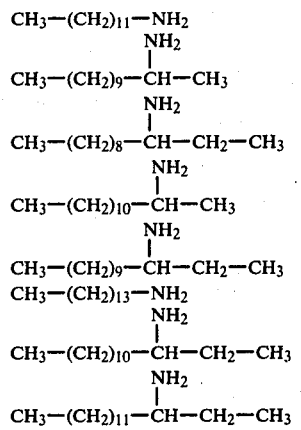

Aminododecane is to be emphasized on account of its particularly good action against coccidial occysts.

The compounds of the formula I can be obtained for example by methods known in the art or by methods analogous thereto, by reaction of an aldehyde or ketone with formamide and formic acid (Organic Reactions V, Ed. John Wiley & Sons, 1949, 301–330; J. Org. Chem. 33, 1968, 1647–1649) or with hydroxylamine hydrochloride in alkaline solution and catalytic reduction of the resultant oxime (J. Org. Chem. 37, 1972, 335–336, J. Chem. Soc. (C), 1966, 531–532).

EXAMPLE 1

Preparation of 2-aminotridecane (a) 70 g of methyl undecyl ketone are added to 250 ml of formamide. The mixture is heated, with constant stirring, to 160° C. Then 40 ml of formic acid are added dropwise in the course of 24 hours. The reaction mixture is cooled, poured on ice, extracted with ether and the ethereal extract is dried over $Na_2SO_4$. After distilling off the ether, the oily residue is distilled in vacuo, affording 60 g of 2-formamidotridecane. Boiling point: 145°–155° C./0.01.

(b) 60 g of 2-formamidotridecane are refluxed in 400 ml of 2 N HCl for 6 hours. The reaction mixture is then cooled in an ice bath, made alkaline with conc. NaOH, extracted with ether, and the ethereal extract is dried over $Na_2SO_4$. The ether is distilled off and the residue is then distilled in vacuo, affording 40 g of 2-aminotridecane. Boiling point: 68°–71° C./0.05.

EXAMPLE 2

Preparation of 2-aminotridecane (a) A solution of 40 g of methyl undecyl ketone and 18 g of hydroxylamino hydrochloride in 200 ml of ethanol, 60 ml of water and 10 g of NaOH is refluxed for 5 hours and thereafter cooled. The ethanol is distilled off in vacuo and the reaction mixture is then diluted with water, extracted with ether and the ethereal extract is dried over $Na_2SO_4$. The ether is distilled off and the solid residue is then distilled in vacuo, affording 40 g of 2-tridecanone oxime. Melting point (after recrystallisation from ether); 51°–53° C.

(b) 20 g of 2-tridecanone oxime are reduced in 200 ml of abs. ethanol with 2 g of 5% palladium on charcoal, affording 16 g of 2-aminotridecane. Boiling point: 82°–87° C./0.01.

The following compounds were prepared by a method analogous to one of the foregoing:

| Compound | Property |
|---|---|
| $CH_3-(CH_2)_7-CH(NH_2)-CH_2-CH_2-CH_3$ | $n_D^{20.5}$ 1.4508 |
| $CH_3-(CH_2)_6-CH(NH_2)-(CH_2)_3-CH_3$ | $n_D^{20.5}$ 1.4489 |
| $CH_3-(CH_2)_{10}-CH(NH_2)-(CH_2)_{10}-CH_3$ | m.p. 74–75° C. |
| $CH_3-(CH_2)_7-CH(NH_2)-CH_2-CH_3$ | b.p. 102–105° C./14 |
| $CH_3-(CH_2)_{10}-CH(NH_2)-CH_2-CH_3$ | b.p. 145–147° C./14 |
| $CH_3-(CH_2)_{11}-CH(NH_2)-CH_2-CH_3$ | b.p. 158–159° C./14 |
| $CH_3-(CH_2)_7-CH(NH_2)-CH_3$ | b.p. 85–87° C./14 |
| $CH_3-(CH_2)_6-CH(NH_2)-CH_2-CH_2-CH_3$ | b.p. 100–105° C./14 |
| $CH_3-(CH_2)_5-CH(NH_2)-CH_2-CH_3$ | b.p. 74–75° C./14 |
| $CH_3-(CH_2)_5-CH(NH_2)-CH_2-CH_2-CH_3$ | b.p. 85–87° C./14 |
| $CH_3-(CH_2)_6-CH(NH_2)-CH_2-CH_3$ | b.p. 84–87° C./14 |
| $CH_3-(CH_2)_9-CH(NH_2)-CH_2-CH_3$ | b.p. 132–136° C./14 |
| $CH_3-(CH_2)_8-CH(NH_2)-CH_2-CH_3$ | b.p. 70–73° C./0.01 |
| $CH_3-(CH_2)_8-CH(NH_2)-CH_3$ | b.p. 50–60° C./0.05 |
| $CH_3-(CH_2)_9-CH(NH_2)-CH_3$ | b.p. 124° C./20 |
| $CH_3-(CH_2)_{11}-NH_2$ | m.p. 28–30° C. |
| $(CH_3)_2CH-CH_2-CH_2-CH(NH_2)-CH_2-CH_2-CH(CH_3)_2$ | b.p. (64–66° C./0.05) |
| $CH_3-(CH_2)_4-CH(NH_2)-CH(CH_3)_2$ | b.p. 94–97° C./13<br>b.p. 68–72° C./13 |
| $CH_3-(CH_2)_9-NH_2$ | m.p. 15–17° C.<br>b.p. 216–218° C.<br>b.p. 98–100° C./11 |
| $CH_3-(CH_2)_{13}-NH_2$ | m.p. 36–38° C.<br>b.p. 162–165° C./15<br>$D_4^{20}$ 0.77 |
| $(CH_3)_2CH-(CH_2)_3-CH(NH_2)-CH_3$ | |
| $CH_3-(CH_2)_{10}-CH(NH_2)-CH(CH_3)_2$ | b.p. 97–99° C./0.05 |
| $CH_3-(CH_2)_{12}-NH_2$ | m.p. 26–29° C. |
| $CH_3-(CH_2)_{10}-NH_2$ | m.p. 15–17° C.<br>b.p. 125–126° C. |

The anticoccidial and ovolarvicidal compositions of the present invention are prepared in a manner known per se by homogeneously mixing and grinding active substances of the formula I with suitable carriers, with or without the addition of dispersants or solvents which are inert to the active substances. The active substances can be formulated and applied as follows:

Solid formulations: dusts, powders, granules (coated granules, impregnated granules and homogeneous granules);

active substance concentrates which are dispersible in water: powder mixture;

liquid formulations: solutions, pastes (emulsions).

The granular size of the carriers for dusts and powder mixtures is advantageously up to approx. 0.1 mm and for granules between 10 and 500μ (0.01–0.5 mm).

Test of the anticoccidial action on oocysts of *Eimeria tenella*

Chicks are infected with oocysts of a pure strain of *Eimeria tenella*. The chicks are sacrificed 7 days later and the oocysts required for testing are taken from the caeca and cleansed by repeated washing in tap water. For sporulation, the oocysts are kept for 4 weeks in potassium bichromate solution. The treatment is carried out by suspending the oocysts in freshly prepared aqueous dilutions of the compositions which have been processed in accordance with galenic principles. Immediately after they have been exposed for 60 minutes on a shaking apparatus, the oocysts are freed from the treatment solution by repeated washing with tap water.

The rate of sporulation is determined microscopically. The action is determined by infecting each of five two-week-old chicks with 100,000 treated oocysts and dissecting the chicks 12 days later. Mortality, the presence of blood in the excrement, oocyst production and intestinal lesions are used as activity parameters.

The test is carried out with unsporulated oocysts (exposure approx. ½ hour after obtention, sporulation after the treatment) and sporulated oocysts (sporulation before the treatment). The tests showed that the active substances have excellent action against coccidial oocysts. No impairment of the state of health of chicks infected with the treated oocysts was observed. There was virtually no production of oocysts.

Ovicidal test on eggs of *Ascaris suum*

Eggs obtained from the tip of the uterine tube of *Ascaris suum* are suspended in tap water and sprayed on a slide in an amount of approx. 5000/cm$^2$ and allowed to dry.

For tests with non-embryonated eggs, treatment with the substances to be tested is subsequently carried out. For tests with embryonated eggs, the slides with the eggs are kept for 5 weeks at 25° C. in open dishes containing tap water, which is changed 5 times a week, until embryonation has taken place.

For treatment, the substances formulated in accordance with galenic principles are diluted with tap water and the slides containing the eggs are sprayed with a dose of 200 ml/m$^2$.

Ordinary tap water as well as the solvents, surfactants etc. used for the formulation, in corresponding aqueous dilutions, are used as control.

After drying, the slides are put into dishes containing tap water for 5 weeks. On the first day the water is changed 5 times to remove the test substances and later 5 times per week.

For the subsequent activity control in the test on non-embryonated and on embryonated eggs, the percentage of embryonated eggs and of intact embryonation respectively is determined microscopically.

The tests revealed that the active substances have a very good action against Ascarididae eggs.

What we claim is:

1. A method for controlling coccidial diseases in animals which comprises treating oocyst-bearing material excreted by the animal with a compound of the formula:

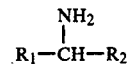

wherein $R_1$ represents alkyl of 4 to 24 carbon atoms and $R_2$ represents hydrogen or alkyl of 1 to 12 carbon atoms, in an effective amount sufficient to kill the oocysts.

2. A method according to claim 1 wherein $R_1$ represents n-alkyl of 7 to 17 carbon atoms and $R_2$ represents hydrogen or alkyl of 1 to 4 carbon atoms.

3. A method according to claim 2, wherein $R_1$ represents n-alkyl of 9 to 13 carbon atoms and $R_2$ represents hydrogen, methyl or ethyl.

4. A method according to claim 3, wherein $R_1$ represents n-alkyl of 9 to 12 carbon atoms and $R_2$ represents methyl or ethyl.

5. A method according to claim 4, wherein $R_1$ represents n-alkyl of 11 to 13 carbon atoms and $R_2$ represents hydrogen.

6. The method according to claim 5 in which the compound is 1-aminododecane.

* * * * *